United States Patent
Mo et al.

(10) Patent No.: US 10,385,404 B2
(45) Date of Patent: Aug. 20, 2019

(54) NRAS GENE MUTATION DETECTION KIT

(71) Applicants: JIAXING ACCB DIAGNOSTICS LTD., Jiaxing (CN); Minli Mo, Beijing (CN); Hui Li, Beijing (CN); Zhao Chen, Beijing (CN); Feng Ding, Beijing (CN); Jun Li, Beijing (CN)

(72) Inventors: Minli Mo, Beijing (CN); Hui Li, Beijing (CN); Zhao Chen, Beijing (CN); Feng Ding, Beijing (CN); Jun Li, Beijing (CN)

(73) Assignee: Jiaxing ACCB Diagnositc Ltd., Jiaxing, ZJ (CN)

( * ) Notice: Subject to any disclaimer, the term of this patent is extended or adjusted under 35 U.S.C. 154(b) by 0 days.

(21) Appl. No.: 15/314,952

(22) PCT Filed: May 27, 2015

(86) PCT No.: PCT/CN2015/000363
§ 371 (c)(1),
(2) Date: Nov. 30, 2016

(87) PCT Pub. No.: WO2015/180489
PCT Pub. Date: Dec. 3, 2015

(65) Prior Publication Data
US 2017/0198355 A1    Jul. 13, 2017

(30) Foreign Application Priority Data

May 30, 2014  (CN) .......................... 2014 1 0234740

(51) Int. Cl.
| | | |
|---|---|---|
| *C07H 21/02* | (2006.01) | |
| *C07H 21/04* | (2006.01) | |
| *C12Q 1/6886* | (2018.01) | |
| *C12Q 1/68* | (2018.01) | |
| *C12Q 1/6848* | (2018.01) | |
| *C12Q 1/6858* | (2018.01) | |

(52) U.S. Cl.
CPC .............. *C12Q 1/6886* (2013.01); *C12Q 1/68* (2013.01); *C12Q 1/6848* (2013.01); *C12Q 1/6858* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2013/0177946 A1* 7/2013 Chen .................... C12Q 1/6848
435/91.2
2013/0217115 A1* 8/2013 Xu ........................ C12Q 1/6851
435/320.1

* cited by examiner

*Primary Examiner* — Carla J Myers
(74) *Attorney, Agent, or Firm* — George G. Wang; Bei & Ocean

(57) ABSTRACT

This invention relates to a kit for detecting NRAS gene mutation, and this kit can be used to detect cancer-related NRAS gene mutation. The said kit comprises: (1) the internal reference detection reagent, which includes the internal reference gene specific primers, internal reference gene specific probes and dNTP solution; (2) the NRAS mutation detection reagent, which includes the NRAS gene mutant type specific primers, NRAS gene mutant type specific probes, internal control gene specific primers, internal control gene specific probes and dNTP solution; (3) the Taq DNA polymerase; and (4) the NRAS positive quality control.

2 Claims, 4 Drawing Sheets
Specification includes a Sequence Listing.

NRAS GENE MUTATION DETECTION KIT

TECHNICAL FIELD

This invention relates to gene mutation detection. Specifically, this invention relates to a kit for detecting NRAS gene mutation, and this kit can be used to detect cancer-related NRAS gene mutation.

BACKGROUND OF THE INVENTION

The Ras gene is a protooncogene, first obtained by cloning from Harvey, Kirsten rat sarcoma, referred to as HRas and KRas[1]. Later, another similar gene was found when the human neuroblastoma DNA infected the NIH3T3 cell, and it was called NRas, and the three are the most important members of the Ras gene family[2]. In function, the Ras protein plays the role as a molecular switch, and can regulate the growth of cells under normal expression. Abnormal conditions such as point mutation, overexpression or gene translocation can lead to abnormal proliferation of cells, and finally result in the formation of tumor. Ras mutation exists in over 30% of human tumors[3, 4]. Presently, the most deeply researched is KRas, and its overexpression and mutation generally occur in many cancers such as thyroid cancer, breast cancer, and among the North American pulmonary granule cancer patients, the mutation rate is as high as 25%. Also, KRas is related to TKI resistance, therefore it has become the molecular mark in the diagnosis and treatment of many tumors, playing an important clinical role[5, 6]. As another member of the Ras family, NRas has many similarities to KRas in both structure and function, and with the deepening of researches in recent years, it has gradually become another molecular indicator serves as an important basis for clinical disease evaluation and treatment besides the KRas.

The NRas gene locates on the short arm of human Chromosome 1 (1p22-p32), encodes p21 protein having 189 amino acids[7]. The NRas proteins has a homology as high as 85% with other proteins in the Ras family, and these highly conservative structure domains include those playing an extremely important role in the function of protein, such as the binding domain of the guanosine triphosphate (GTP) and the effector molecules, and the CAAX sequence motif that positions the NRas protein on the farnesyl transferase acting site—C end on the plasmalemma[8, 9]. Therefore, functionally, NRas also has many common features of the RAS family proteins: it locates on the inside of the cell membrane, and is a G protein of low molecular weight, with very strong affinity to guanylic acid, and having GTPase activity; it has two conformations of GTP binding (Ras.GTP) and GDP binding (Ras.GDP), and interconversion can take place of the two under certain conditions; the Ras protein is in the inactivated state when binds with GDP, and in the activated state when binds with GTP, such that it activates the downstream signal pathway, so it plays an extremely important switching role in the signal transduction[10, 11]. The downstream signal pathway activated by NRas is now the RAS signal pathway having been most clearly researched currently: the PTK (protein tyrosine kinase)-Grb2 (growth factor receptor-bound protein2)-Ras-Raf-MAPK (mitogen activated protein kinase)-ERK (extracellular signal-regulated kinase) pathway[12]. When exogenous stimulus such as growth factor (EGF) is bound with cell membrane receptor (EGFR), so that the corresponding tyrosine kinase on the receptor is phosphorylated, the phosphorylated tyrosine residue, after binding with the SH2 zone of Grb2, recruits the ornithine exchange factor (SOS) to bind with the SH3 zone of Grb2, to form the complex Grb2-SOS, and this complex binds with Ras and converts Ras-GDP into Ras-GTP, thus activating the Ras. The activated Ras then activates the downstream Raf kinase, the Raf kinase phosphorylates MAPK, the MAPK activates the ERK. After the ERK is activated, it transfers to inside the cell nucleus, directly activating various transcription factors of c-myc, so as to participate in various physiological processes such as cell growth, development, division and differentiation[13]. Mutation of NRas can lead to abnormal activation of the downstream Raf and MAPK etc., thus playing an important role in the tumor malignance[14].

Mutation of Ras protein mainly occurs on Codons 12, 13, 59 and 61, and the mutation probability is the highest on Codons 12 and 61[15]. The mutation is of different types in different cancers. In non-small cell lung cancer, the main mutation is the guanine in Codon 12 is replaced by thymine, while in colon cancer, at the same position, mainly the guanine is replaced by adenine[16]. NRas mutation mainly occurs at Codon 61, with high probability in melanoma. Thoams et al used the "mutation" and "melanoma" as key words to retrieve and analyze articles published in the pubmed during 1966-2006, and found a NRas mutation rate as high as 28% in surface diffused and nodositas melanoma[17]. Vikas et al found 10 cases of NRas mutation (17%, 10/16) in 60 cases of primary melanoma, and all mutations occur at Codon 61[18]. It is worth our high attention that in recent years, NRas has been confirmed as the driver gene of lung cancer. Kris et al published on ASCO in 2011 a research from LCMC (NCI's Lung Cancer Mutation Consortium), in which the 10 driver genes including KRas, EGFR and NRas etc. in 1000 pulmonary granule cancer tissue specimens were tested. All patients were of phases IIIb/IV, with sufficient tissue specimens. The research included 830 patients, 60% patients had driver gene mutation, and the mutation rate of NRas was 0.2%[19, 20].

As the effect of Ras mutation on tumors is mostly concentrated on the Ras/Raf/MEK/ERK pathway, therefore today, the targeted antitumor drugs against Ras mutation are concentrated on the targeted intervention at different nodes in this signal pathway. The developed drugs include the farnesyl transferase inhibitors (FTIs) that intervene with the Ras membrane binding and lypolyzation, such as tipifarnib[21], ATP indirect competitor sorafenib for activation of Raf[22, 23], and CI-1040 and AZD6244 for MEK targeted intervention, and the latter have already been used in clinical test[24]. As ERK is the only substrate of MEK known today, and it is usually described as the single pathway downstream the Ras, therefore it is generally believed that inhibition solely at the MEK target point is equal to blocking the ERK activation caused by the mutated Ras, and it can also avoid the effect of invalid targeting caused by the interference from other pathways[9].

It should be particularly pointed out that, the latest researches have indicated that the NRas mutation is related to the TKI resistance in the treatment of lung cancer. Compared with the gefitinib sensitive PC-9 cell (PC-9/WT), no EGFR-TKIs resistance gene such as KRas and HER2 were detected in PC-9 cell (PC-9/gef) where gefitinib resistance was produced, but NRas mutation at Codon 61 was found. Moreover, in the condition that an administration of gefitinib or AZD6244/CI1040 only could not make cell apoptosis, the combined use of both drugs can effectively promote cell apoptosis[25]. These experimental results have indicated that NRas mutation may play an important role in the TKI resistance in lung cancer treatment, and this has provided new basis and possibility for the detection and treatment of lung cancer.

In general, more and more evidences have shown that NRas mutation has important significance in the occurrence and development of many human tumors such as melanoma and lung cancer. The detection of its mutation enables accurately prediction of the effectiveness of the corresponding targeted drug treatment, so as to facilitate clinical selection of drugs, effectively improve treatment results and provide the maximum benefit to patients; in the meanwhile, it can also avoid medical expense burden on patients and waste of public medical resources resulted from unreasonable application of drugs, and reduce unnecessary loss of time and money losses.

SUMMARY OF THE INVENTION

In this invention, the kit for detecting has been designed for the following detection sites:

TABLE 1

| | Mutation detection sites | | | |
|---|---|---|---|---|
| No. | gene IR gene ACTB | mutation position | mutated base | mutated amino acid |
| NM1 | NRAS | Codon 12 | 34G > A | G12S |
| NM2 | NRAS | Codon 12 | 35G > A | G12D |
| NM3 | NRAS | Codon 13 | 38G > A | G13D |
| NM4 | NRAS | Codon 61 | 181C > A | Q61K |
| NM5 | NRAS | Codon 61 | 182A > T | Q61L |
| NM6 | NRAS | Codon 61 | 182A > G | Q61R |
| NM7 | NRAS | Codon 61 | 183A > T | Q61H |

Specifically, the present invention relates to a kit for detecting NRAS gene mutation, comprising:

(1) internal reference detection reagent, which includes the internal reference gene specific primers, internal reference gene specific probes and dNTP solution;

(2) NRAS mutation detection reagent, which includes the NRAS gene mutant type specific primers, NRAS gene mutant type specific probes, internal control gene specific primers, internal control gene specific probes and dNTP solution;

(3) Taq DNA polymerase; and (4) NRAS positive quality control (PC), which includes the internal reference gene, NRAS gene mutant type and internal control gene fragments.

More specifically, in the above-mentioned kit, internal reference gene specific primers in the said internal reference detection reagent are SEQ ID No: 1 and SEQ ID No: 2; in the said internal reference detection reagent, the IR gene specific probe is SEQ ID No: 16; the NRAS gene mutant type in the said NRAS mutation detection reagent is NM1, i.e. NRAS gene 12 codon 34G>A; NM2, i.e. NRAS gene 12 codon 35G>A; NM3, i.e. NRAS gene 13 codon 38G>A; NM4, i.e. NRAS gene 61 codon 181C>A; NM5, i.e. NRAS gene 61 codon 182A>T; NM6, i.e. NRAS gene 61 codon 182A>G; or NM7, i.e. NRAS gene 61 codon 183A>T. The reagent kit of this invention can be used to detect at least one mutation of NM1, NM2, NM3, NM4, NM5, NM6 and NM7.

In the said NRAS mutation detection reagent, the NRAS gene mutant type specific primers are as follows: for NM1 mutation the primers are SEQ ID No: 5 and SEQ ID No: 8; for NM2 mutation the primers are SEQ ID No: 6 and SEQ ID No: 8; for NM3 mutation the primers are SEQ ID No: 7 and SEQ ID No: 8; for NM4 mutation the primers are SEQ ID No: 9 and SEQ ID No: 13; for NM5 mutation the primers are SEQ ID No: 10 and SEQ ID No: 13; for NM6 mutation the primers are SEQ ID No: 11 and SEQ ID No: 13; for NM7 mutation the primers are SEQ ID No: 12 and SEQ ID No: 13; in the said NRAS mutation detection reagent the NRAS gene mutant type specific probes are selected from SEQ ID No: 14 or SEQ ID No: 15; in the said NRAS mutation detection reagent the internal control gene specific primers are SEQ ID No: 3 and SEQ ID No: 4; in the said NRAS mutation detection reagent the internal control gene specific probe is SEQ ID No: 17; the end concentration of the said dNTP solution is 400 μM; the said IR gene sequence is SEQ ID No: 18; the said internal control gene sequence is SEQ ID No: 19; and the sequence of said NRAS gene is SEQ ID No: 20 or SEQ ID No: 21.

EXAMPLES

1. Experiment Method

Figure 1:
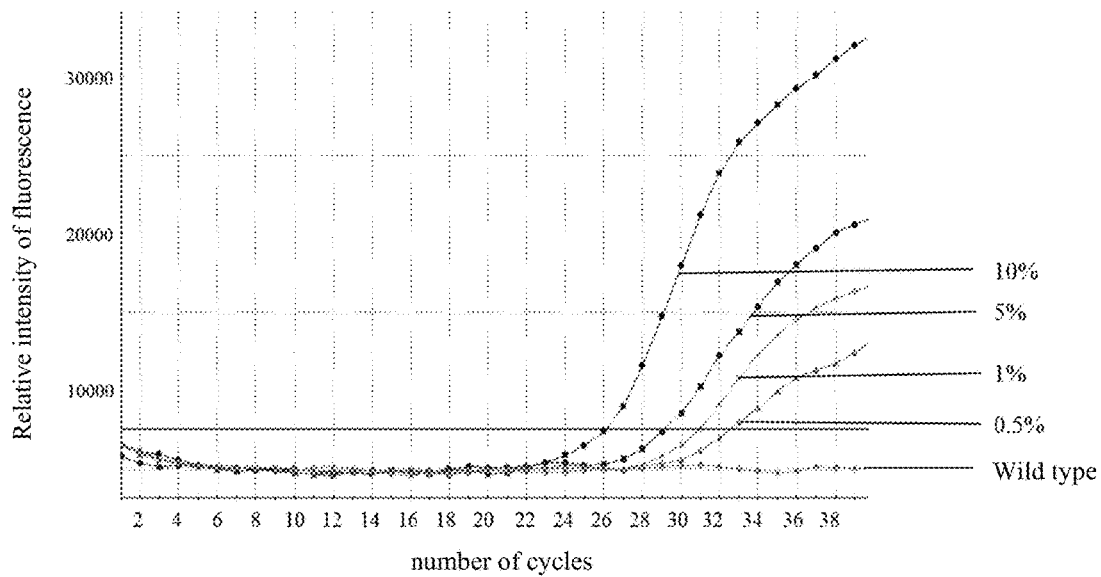
FIG. 1 shows the result of NM1 mutation detection, in which the content of the wild type genome DNA is 20 ng/μl, the content of mutant genome DNA is 10 ng/μl, and respectively contains 10, 5, 1, 0.5% mutation.

The real-time fluorescent PCR technology was adopted. The ARMS (amplification refractory mutation system) method was used to detect gene mutation. That is, gene mutation was detected by using primers 3' end to identify mutation, in conjunction with the TaqMan probe hydrolysis luminescence.

The kit includes the internal reference (IR) detection and internal control (IC) detection. The IR gene is a housekeeping gene different from the NRAS gene to be tested. By detecting the amplification of the IR gene (FAM channel), analysis can be made whether the DNA to be tested can be normally amplified, so as to exclude causes of PCR detection failure such as poor DNA purity and concentration, or containing PCR inhibitor. In this kit, the IC detection system is also provided in the detection systems for various mutation types of NRAS gene. The two systems react in the same PCR tube at the same time. The IC gene is also a housekeeping gene different from the NRAS gene to be tested. The probe identifying the NRAS gene mutant template was modified with a FAM fluorescent radical, and the probe identifying the IC gene template was modified with the HEX fluorescent radical. By detecting the amplification of the IC gene (HEX channel), analysis can be made whether the DNA to be tested can be normally amplified, so as to exclude causes of PCR detection failure such as missing reagent or specimen, or specimen containing PCR inhibitor.

2. Composition of Reagent Kit (Table 2)

| name | components |
|---|---|
| IR detection reagent | including the internal reference gene (housekeeping gene different from the NRAS gene to be tested) specific primers, probe and dNTP solution; |
| NRAS mutation detection reagent | including NRAS gene mutant type, internal control gene specific primers, probe and dNTP solution |
| Taq DNA polymerase | Taq DNA polymerase |
| NRAS positive quality control (PC) | including internal reference gene, NRAS gene mutant type and internal control gene fragment |

2.1 IR, NM1~7 Detection Reagent, Taq DNA Polymerase (Table 3):

| name of raw material | source of raw material | end concentration in the detection system |
|---|---|---|
| Taq enzyme buffer | Tiangen | 1× |
| Magnesium chloride | Tiangen | 3 mM |
| dNTP (containing dATP, dTTP, dCTP, dGTP) | Tiangen | 400 μM |
| Forward primer | Shenggong | 500 nM |
| Reverse primer | Shenggong | 500 nM |
| Probe | Shenggong | 300 nM |
| Taq DNA polymerase | Tiangen | 0.05/μl |

2.2 Positive Quality Control PC:
Artificially cloned on the pMD18T plasmid.
2.3 Primer and Probe Sequences (Table 4):

The internal reference gene and internal control gene fragments in NRAS positive quality control (PC) can be obtained from for example the NCBI nucleotide database (http://www.ncbi.nlm.nih.gov/nuccore). For example, through the accession No. NG_007992.1, we can obtain the amplified fragment of internal reference gene (IR):

(SEQ ID No: 18)
CAGATGTGGATCAGCAAGCAGGAGTATGACGAGTCCGGCCCCTCCATCGT
CCACCGCAAATGCTTCTAGGCGGACTATG and the amplified fragment of internal control gene (IC)

(SEQ ID No: 19)
GATCAGCAAGCAGGAGTATGACGAGTCCGGCCCCTCCATCGTCCACCGCA
AATGCTTCTAGGCGGACTATGACTTAGTTGCGTTACACC.

From this database, we can also obtain the amplified fragment of NRAS containing Codon 12 and 13

(SEQ ID No: 20)
GGTGGTGGTTGGAGCAGGTGGTGTTGGGAAAAGCGCACTGACAATCCA
GCTAATCCAGAACCACTTTGTAGATGAATATGATCCCACCATAGAGGTGA

Condon 12 and 13 are shown in boxes.
From this database, we can also obtain the amplified fragment of NRAS containing Codon 61:

(SEQ ID No: 21)
ATACTGGATACAGCTGGACAAGAAGAGTACAGTGCCATGAGAGACCAATAC
ATGAGGACAGGCGAAGGCTTCCTCTGTG

Condon 61 is shown in box.

Figure 2:
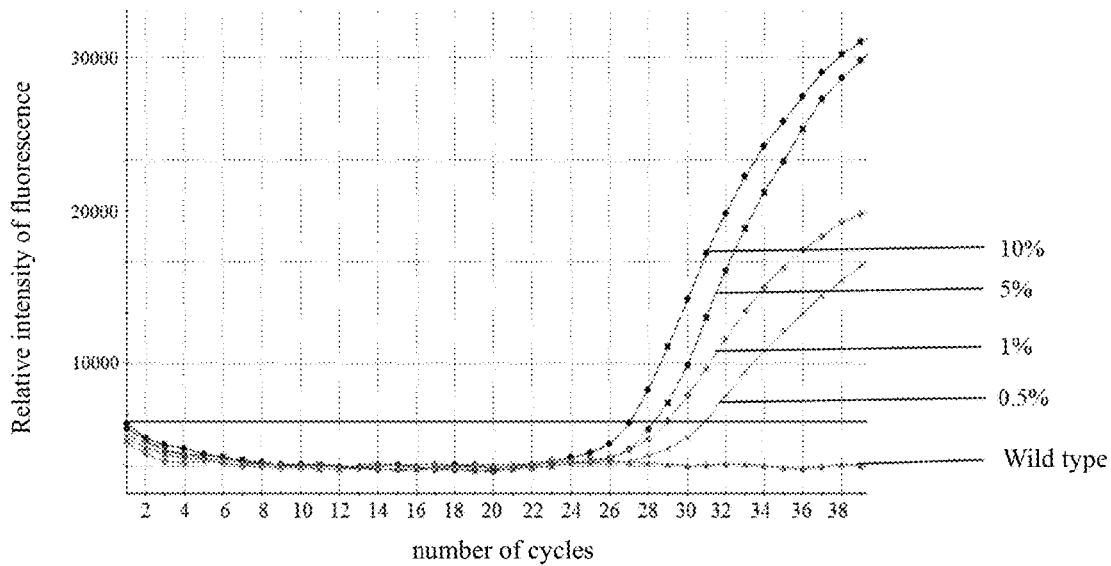
FIG. 2 shows the result of NM2 mutation detection, in which the content of the wild type genome DNA is 20 ng/μl, the content of mutant genome DNA is 10 ng/μl, and respectively contains 10, 5, 1, 0.5% mutation.
Figure 3:
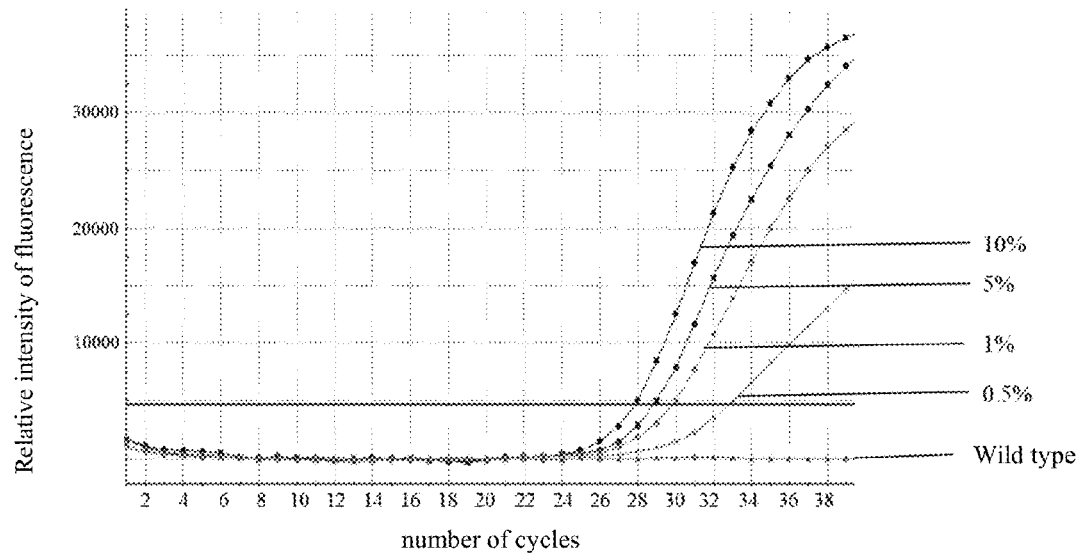
FIG. 3 shows the result of NM3 mutation detection, in which the content of the wild type genome DNA is 20 ng/μl, the content of mutant genome DNA is 10 ng/μl, and respectively contains 10, 5, 1, 0.5% mutation.
Figure 4:
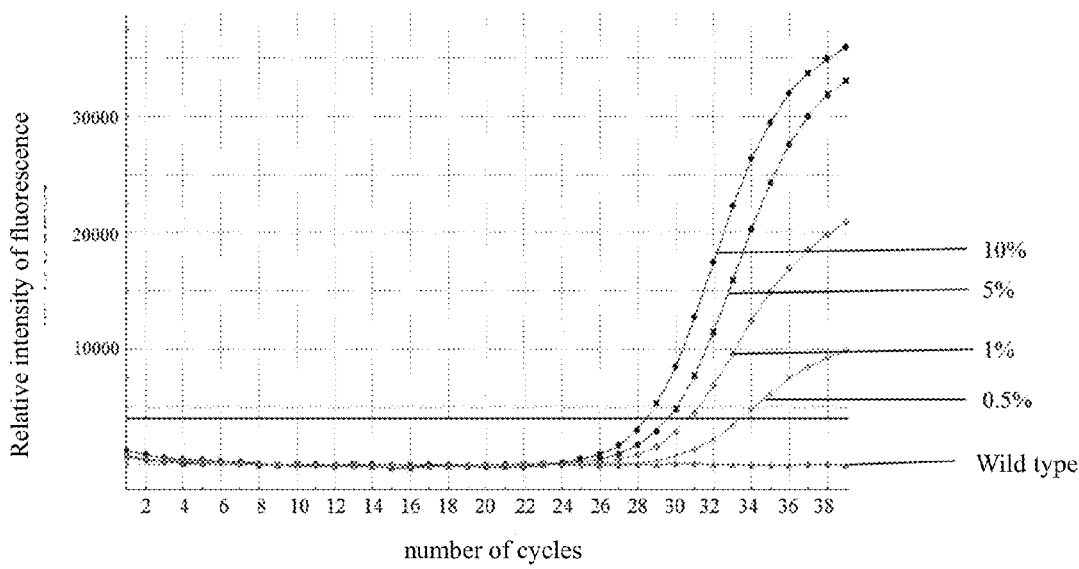
FIG. 4 shows the result of NM4 mutation detection, in which the content of the wild type genome DNA is 20 ng/μl, the content of mutant genome DNA is 10 ng/μl, and respectively contains 10, 5, 1, 0.5% mutation.
Figure 5:
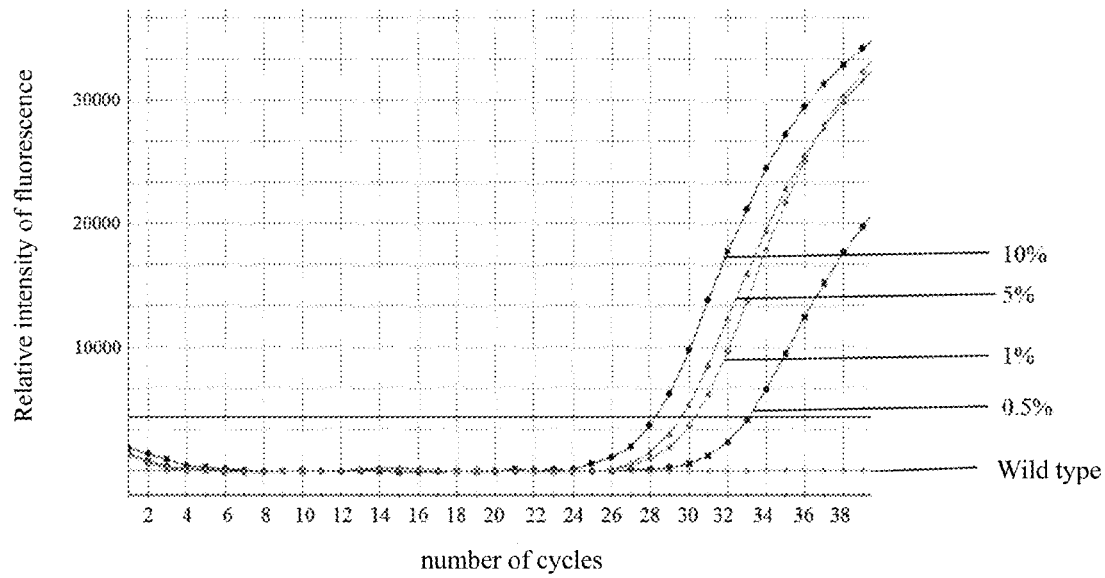
FIG. 5 shows the result of NM5 mutation detection, in which the content of the wild type genome DNA is 20 ng/μl, the content of mutant genome DNA is 10 ng/μl, and respectively contains 10, 5, 1, 0.5% mutation.
Figure 6:
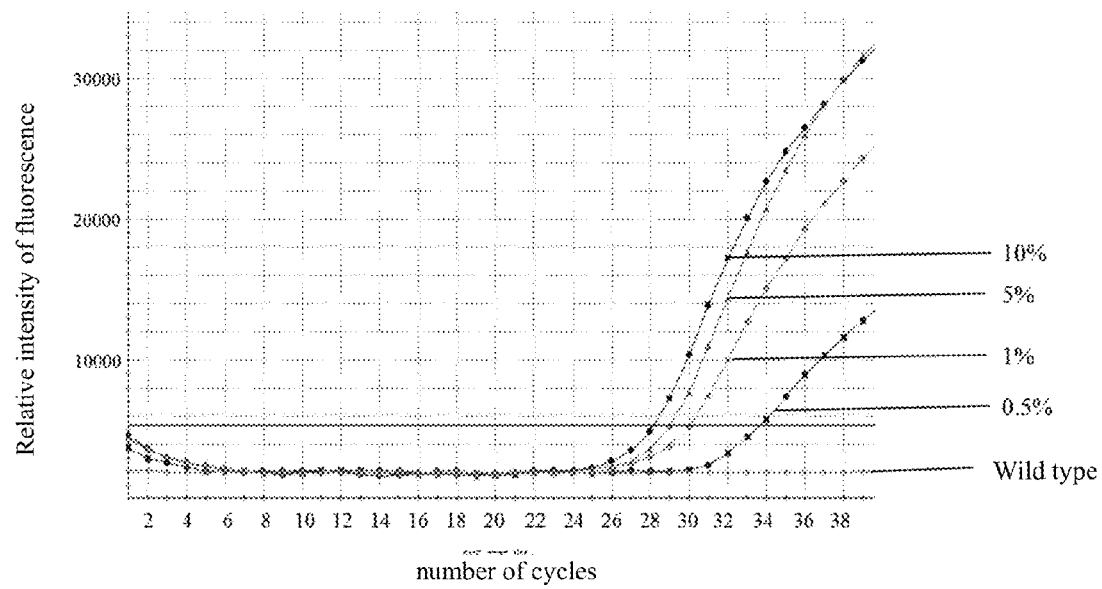
FIG. 6 shows the result of NM6 mutation detection, in which the content of the wild type genome DNA is 20 ng/μl, the content of mutant genome DNA is 10 ng/μl, and respectively contains 10, 5, 1, 0.5% mutation.
Figure 7:
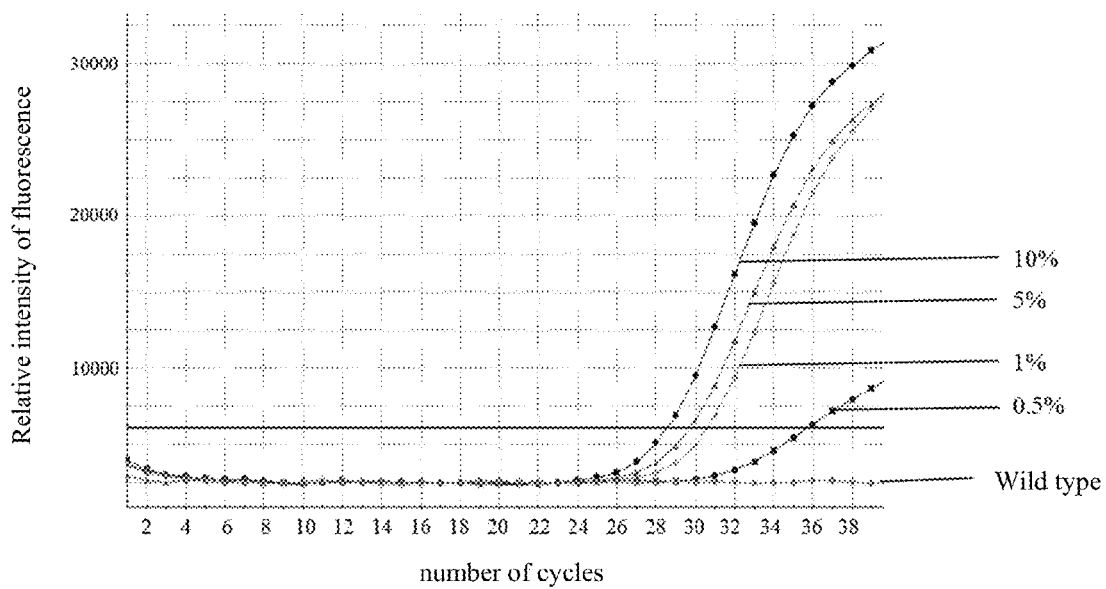
FIG. 7 shows the result of NM7 mutation detection, in which the content of the wild type genome DNA is 20 ng/μl, the content of mutant genome DNA is 10 ng/μl, and respectively contains 10, 5, 1, 0.5% mutation.

3. Embodiments 3.1 Specificity and Sensitivity:
We detected 20 ng/μl genome DNA containing wild type NRAS only, and 10 ng/μl genome DNA containing 10, 5, 1, 0.5% NRAS mutation respectively (mutation percentage=mutant type/wild type×100%). The experiment result is presented in FIG. 1-7.

| classification | name | sequence (5'-3') | SEQ ID No: |
|---|---|---|---|
| primers | IR-F | CAGATGTGGATCAGCAAGCA | 1 |
| | IR-R | CATAGTCCGCCTAGAAGCATT | 2 |
| | IC-F | GATCAGCAAGCAGGAGTAT | 3 |
| | IC-R | GGTGTAACGCAACTAAGTC | 4 |
| | NM1-F | GGTGGTGGTTGGAGCAA | 5 |
| | NM2-F | GTGGTGGTTGGAGCAGA | 6 |
| | NM3-F | GTGGTTGGAGCAGGTGA | 7 |
| | NM123-R | TCACCTCTATGGTGGGATCAT | 8 |
| | NM4-F | ATACTGGATACAGCTGGAA | 9 |
| | NM5-F | TACTGGATACAGCTGGACT | 10 |
| | NM6-F | TACTGGATACAGCTGGACG | 11 |
| | NM7-F | TACTGGATACAGCTGGACAT | 12 |
| | NM4567-R | CACAGAGGAAGCCTTCGCCT | 13 |
| probes | NM123-pb | AGCGCACTGACAATCCAGCTAATC (5'-FAM, 3'-BHQ1) | 14 |
| | NM4567-pb | AGAGTACAGTGCCATGAGAGACC (5'-FAM, 3'-BHQ1) | 15 |
| | IR-pb | ATGACGAGTCCGGCCCCTCCATC (5'-FAM, 3'-BHQ1) | 16 |
| | IC-pb | TAGTCCGCCTAGAAGCATTTGC (5'-HEX, 3'-BHQ1) | 17 |

3.2 Comparison of Methods (the Kit of the Present Invention and the Sequencing Method):

TABLE 5

The kit of the present invention and the test result of Sanger sequencing method with four-fold table method

|  |  | Sanger sequencing method | |
| --- | --- | --- | --- |
|  |  | positive (mutant type) | negative (wild type) |
| kit of the present invention | positive (mutant type) | 3 | 1 |
|  | negative (wild type) | 0 | 196 |

It includes 100 cases each for lung cancer and colorectal cancer

The four-fold table method is a means to analyze the Receiver Operating Characteristic (ROC) which is familiar to the technical person in this art.

If the Sanger sequencing method is taken as the "gold standard" for testing gene mutation, then it can be obtained by calculation from Table 5 that: the clinical sensitivity of NRAS kit=3/(3+0)=100%, its clinical specificity=196/(1+196)=99.5%, and overall consistency=(3+196)/(3+196+1+0)=99.5%. This shows that the kit of the present invention has very high clinical sensitivity, clinical specificity and overall consistency.

In addition, it can be seen from the data of the four-fold table that, all specimens shown positive with Sanger sequencing method are positive when detected with quantitative PCR (QPCR), but specimens detected as positive with QPCR can be detected as negative with the Sanger sequencing method, indicating that the QPCR kit of the present invention has a higher sensitivity than that of the Sanger sequencing method.

REFERENCES

[1] Ellis R W, DeFeo D, Furth M E, et al. Mouse cells contain two distinct ras gene mRNA species that can be translated into a p21 one protein[J]. Mol Cell Biol, 1982, 2(11): 1339-1345.
[2] Stacey D W, Kung H F. Transformation of NIH 3T3 cells by microinjection of Ha-ras p21 protein[J]. Nature, 1984, 310(5977): 508-511.
[3] Baines A T, Xu D, Der C J. Inhibition of Ras for cancer treatment: the search continues[J]. Future Med Chem, 2011, 3(14): 1787-1808.
[4] Overmeyer J H, Maltese W A. Death pathways triggered by activated Ras in cancer cells[J]. Front Biosci (Landmark Ed), 2011, 16: 1693-1713.
[5] Shigematsu H, Gazdar A F. Somatic mutations of epidermal growth factor receptor signaling pathway in lung cancers[J]. Int J Cancer, 2006, 118(2): 257-262.
[6] Eberhard D A, Johnson B E, Amler L C, et al. Mutations in the epidermal growth factor receptor and in KRAS are predictive and prognostic indicators in patients with non-small-cell lung cancer treated with chemotherapy alone and in combination with erlotinib[J]. J Clin Oncol, 2005, 23(25): 5900-5909.
[7] Rabin M, Watson M, Barker P E, et al. NRAS transforming gene maps to region p11----p13 on chromosome 1 by in situ hybridization[J]. Cytogenet Cell Genet, 1984, 38(1): 70-72.
[8] Chetty R, Govender D. Gene of the month: KRAS[J]. J Clin Pathol, 2013, 66(7): 548-550.
[9] Chang Yu Sui Liu, Fu Huaqun, Yu Bengtong, Zou Shubing, Wu Qicai and Wan Li, Role of Ras/Raf/MEK/ERK Pathway in the Drug Targeting Therapy of Esophagus Cancer [J]. Acta Pharmaceutica Sinica, 2013, 48(5): 635-641.
[10] Shih T Y, Hattori S, Clanton D J, et al. Structure and function of p21 ras proteins[J]. Gene Amplif Anal, 1986, 4: 53-72.
[11] Lacal J C, Anderson P S, Aaronson S A. Deletion mutants of Harvey ras p21 protein reveal the absolute requirement of at least two distant regions for GTP-binding and transforming activities[J]. EMBO J, 1986, 5(4): 679-687.
[12] Marais R, Marshall C J. Control of the ERK MAP kinase cascade by Ras and Raf[J]. Cancer Surv, 1996, 27: 101-125.
[13] Andresen B T, Rizzo M A, Shome K, et al. The role of phosphatidic acid in the regulation of the Ras/MEK/Erk signaling cascade[J]. FEBS Lett, 2002, 531(1): 65-68.
[14] Bauer J, Curtin J A, Pinkel D, et al. Congenital melanocytic nevi frequently harbor NRAS mutations but no BRAF mutations[J]. J Invest Dermatol, 2007, 127(1): 179-182.
[15] Smit V T, Boot A J, Smits A M, et al. KRAS codon 12 mutations occur very frequently in pancreatic adenocarcinomas[J]. Nucleic Acids Res, 1988, 16(16): 7773-7782.
[16] He Taiping and Yan Weihong. Ras Signal Pathway Transduction [J]. Foreign Medicine Clinical Biochemistry and Ecsomatics Volume, 2004, 25(1): 74-76.
[17] Hocker T, Tsao H. Ultraviolet radiation and melanoma: a systematic review and analysis of reported sequence variants[J]. Hum Mutat, 2007, 28(6): 578-588.
[18] Goel V K, Lazar A J, Warneke C L, et al. Examination of mutations in BRAF, NRAS, and PTEN in primary cutaneous melanoma[J]. J Invest Dermatol, 2006, 126(1): 154-160.
[19] Kris M G J B, Kwiatkowski D G, et al. Identification of driver mutations in tumor specimens from 1,000 patients with lung adenocarcinoma[J]. The NCI's Lung Cancer Mutation Consortium (LCMC) J Clin Oncol, 2011, 29(18): abstract 7506.
[20] Wang Jinghui, Zhang Zongde and Zhang Shucai. Relevant Progress in Research of Pulmonary Granule Cancer Driver Genes [J]. China Lung Cancer Journal, 2013, 16(2): 91-96.
[21] Medeiros B C, Landau H J, Morrow M, et al. The farnesyl transferase inhibitor, tipifarnib, is a potent inhibitor of the MDR1 gene product, P-glycoprotein, and demonstrates significant cytotoxic synergism against human leukemia cell lines[J]. Leukemia, 2007, 21(4): 739-746.
[22] Jiang Chengying. Action Mechanism of RasRaf MekErk Signal Conduction Pathway in the Occurrence of Hepatocellular Carcinoma and its Application in the Targeted Treatment [J]. Chinese Journal of Clinical Oncology, 2008, 35(23): 1377-1380.
[23] Keswani R N, Chumsangsri A, Mustafi R, et al. Sorafenib inhibits MAPK-mediated proliferation in a Barrett's esophageal adenocarcinoma cell line[J]. Dis Esophagus, 2008, 21(6): 514-521.
[24] Martin T D, Samuel J C, Routh E D, et al. Activation and involvement of Ral GTPases in colorectal cancer[J]. Cancer Res, 2011, 71(1): 206-215.
[25] Huang M H, Lee J H, Chang Y J, et al. MEK inhibitors reverse resistance in epidermal growth factor receptor mutation lung cancer cells with acquired resistance to gefitinib[J]. Mol Oncol, 2013, 7(1): 112-120.

The invention claimed is:

1. A kit for detecting NRAS gene mutation, comprising:
   (1) internal reference detection reagent, which includes the internal reference gene specific primers, internal reference gene specific probes and a first dNTP solution,
   in which the said internal reference gene specific primers are SEQ ID No: 1 and SEQ ID No: 2, and the said internal reference gene specific probe is SEQ ID No: 16;
   (2) NRAS mutation detection reagent, which includes the NRAS gene mutant type specific primers, NRAS gene mutant type specific probes, internal control gene specific primers, internal control gene specific probes and a second dNTP solution,
   in which said NRAS gene mutant type is NM1, i.e. NRAS gene Codon 12 34G>A;
   the NRAS gene mutant type specific primers are SEQ ID No: 5 and SEQ ID No: 8;
   the NRAS gene mutant type specific probe is SEQ ID No: 14;
   the internal control gene specific primers are SEQ ID No: 3 and SEQ ID No: 4; the said internal control gene specific probe is SEQ ID No: 17;
   (3) Taq DNA polymerase; and
   (4) NRAS positive quality control, which includes the internal reference gene, NRAS gene mutant type and internal control gene fragments, in which the sequence of internal reference gene sequence is SEQ ID No: 18; the sequence of internal control gene fragment sequence is SEQ ID No: 19;
   wherein the internal reference specific probe and the internal control gene specific probe are each connected with the FAM radical, and the 3' end connected with the BHQ1 radical.

2. The kit according to claim 1, in which the end concentration of the first and second dNTP solutions are each 400 μM.

* * * * *

SEQUENCE LISTING

<160> NUMBER OF SEQ ID NOS: 21

<210> SEQ ID NO 1
<211> LENGTH: 20
<212> TYPE: DNA
<213> ORGANISM: artificial
<220> FEATURE:
<223> OTHER INFORMATION: internal reference gene specific primer
      (forward primer, IR-F)

<400> SEQUENCE: 1
cagatgtgga tcagcaagca                                               20

<210> SEQ ID NO 2
<211> LENGTH: 21
<212> TYPE: DNA
<213> ORGANISM: artificial
<220> FEATURE:
<223> OTHER INFORMATION: internal reference gene specific primer
      (reverse primer, IR-R)

<400> SEQUENCE: 2
catagtccgc ctagaagcat t                                             21

<210> SEQ ID NO 3
<211> LENGTH: 19
<212> TYPE: DNA
<213> ORGANISM: artificial
<220> FEATURE:
<223> OTHER INFORMATION: internal control gene specific primer
      (forward primer, IC-F)

<400> SEQUENCE: 3
gatcagcaag caggagtat                                                19

<210> SEQ ID NO 4
<211> LENGTH: 19
<212> TYPE: DNA
<213> ORGANISM: artificial
<220> FEATURE:
<223> OTHER INFORMATION: internal control gene specific primer
      (reverse primer, IC-R)

<400> SEQUENCE: 4
ggtgtaacgc aactaagtc                                                19

<210> SEQ ID NO 5
<211> LENGTH: 17
<212> TYPE: DNA
<213> ORGANISM: artificial
<220> FEATURE:
<223> OTHER INFORMATION: NRAS gene mutant type primers (NM1 forward
      primers, NM1-F, NM2)

<400> SEQUENCE: 5
ggtggtggtt ggagcaa                                                  17

<210> SEQ ID NO 6
<211> LENGTH: 17
<212> TYPE: DNA
<213> ORGANISM: artificial
<220> FEATURE:
<223> OTHER INFORMATION: NRAS gene mutant type primers (NM2 forward
      primers, NM2-F, NM5)

<400> SEQUENCE: 6
gtggtggttg gagcaga                                                  17

```
<210> SEQ ID NO 7
<211> LENGTH: 17
<212> TYPE: DNA
<213> ORGANISM: artificial
<220> FEATURE:
<223> OTHER INFORMATION: NRAS gene mutant type primers (NM3 forward
      primers, NM3-F, NM8)

<400> SEQUENCE: 7
gtggttggag caggtga                                                 17

<210> SEQ ID NO 8
<211> LENGTH: 21
<212> TYPE: DNA
<213> ORGANISM: artificial
<220> FEATURE:
<223> OTHER INFORMATION: NRAS gene mutant type primers (NM1, NM2, NM3
      reverse primers, NM123-R)

<400> SEQUENCE: 8
tcacctctat ggtgggatca t                                            21

<210> SEQ ID NO 9
<211> LENGTH: 19
<212> TYPE: DNA
<213> ORGANISM: artificial
<220> FEATURE:
<223> OTHER INFORMATION: NRAS gene mutant type primer (NM4
      forward primer, NM4-F)

<400> SEQUENCE: 9
atactggata cagctggaa                                               19

<210> SEQ ID NO 10
<211> LENGTH: 19
<212> TYPE: DNA
<213> ORGANISM: artificial
<220> FEATURE:
<223> OTHER INFORMATION: NRAS gene mutant type primer (NM5
      forward primer, NM5-F)

<400> SEQUENCE: 10
tactggatac agctggact                                               19

<210> SEQ ID NO 11
<211> LENGTH: 19
<212> TYPE: DNA
<213> ORGANISM: artificial
<220> FEATURE:
<223> OTHER INFORMATION: NRAS gene mutant type primer (NM6
      forward primer, NM6-F)

<400> SEQUENCE: 11
tactggatac agctggacg                                               19

<210> SEQ ID NO 12
<211> LENGTH: 20
<212> TYPE: DNA
<213> ORGANISM: artificial
<220> FEATURE:
<223> OTHER INFORMATION: NRAS gene mutant type primer (NM7
      forward primer, NM7-F)

<400> SEQUENCE: 12
tactggatac agctggacat                                              20
```

<210> SEQ ID NO 13
<211> LENGTH: 20
<212> TYPE: DNA
<213> ORGANISM: artificial
<220> FEATURE:
<223> OTHER INFORMATION: NRAS gene mutant type primers (NM4, NM5, NM6, NM7 reverse primers, NM4567-R)

<400> SEQUENCE: 13
cacagaggaa gccttcgcct                                                  20

<210> SEQ ID NO 14
<211> LENGTH: 24
<212> TYPE: DNA
<213> ORGANISM: artificial
<220> FEATURE:
<223> OTHER INFORMATION: NRAS gene mutant type probes (NM1, NM2, NM3 probes, NM123-pb)

<400> SEQUENCE: 14
agcgcactga caatccagct aatc                                             24

<210> SEQ ID NO 15
<211> LENGTH: 23
<212> TYPE: DNA
<213> ORGANISM: artificial
<220> FEATURE:
<223> OTHER INFORMATION: NRAS gene mutant type probes (NM4, NM5, NM6, NM7 probe, NM4567-pb)

<400> SEQUENCE: 15
agagtacagt gccatgagag acc                                              23

<210> SEQ ID NO 16
<211> LENGTH: 23
<212> TYPE: DNA
<213> ORGANISM: artificial
<220> FEATURE:
<223> OTHER INFORMATION: internal reference gene probe (IR-pb)

<400> SEQUENCE: 16
atgacgagtc cggcccctcc atc                                              23

<210> SEQ ID NO 17
<211> LENGTH: 22
<212> TYPE: DNA
<213> ORGANISM: artificial
<220> FEATURE:
<223> OTHER INFORMATION: internal control gene probe (IC-pb)

<400> SEQUENCE: 17
tagtccgcct agaagcattt gc                                               22

<210> SEQ ID NO 18
<211> LENGTH: 79
<212> TYPE: DNA
<213> ORGANISM: unknown
<220> FEATURE:
<223> OTHER INFORMATION: amplified fragment of internal reference gene (IR)

<400> SEQUENCE: 18
cagatgtgga tcagcaagca ggagtatgac gagtccggcc cctccatcgt ccaccgcaaa      60
tgcttctagg cggactatg                                                   79

```
<210> SEQ ID NO 19
<211> LENGTH: 89
<212> TYPE: DNA
<213> ORGANISM: unknown
<220> FEATURE:
<223> OTHER INFORMATION: amplified fragment of internal control gene
      (IC)

<400> SEQUENCE: 19
gatcagcaag caggagtatg acgagtccgg cccctccatc gtccaccgca aatgcttcta    60
ggcggactat gacttagttg cgttacacc                                      89

<210> SEQ ID NO 20
<211> LENGTH: 98
<212> TYPE: DNA
<213> ORGANISM: unknown
<220> FEATURE:
<223> OTHER INFORMATION: amplified fragment of NRAS (containing Codon
      12, 13)

<400> SEQUENCE: 20
ggtggtggtt ggagcaggtg gtgttgggaa aagcgcactg acaatccagc taatccagaa    60
ccactttgta gatgaatatg atcccaccat agaggtga                            98

<210> SEQ ID NO 21
<211> LENGTH: 79
<212> TYPE: DNA
<213> ORGANISM: unknown
<220> FEATURE:
<223> OTHER INFORMATION: amplified fragment of NRAS (containing Codon
      61)

<400> SEQUENCE: 21
atactggata cagctggaca agaagagtac agtgccatga gagaccaata catgaggaca    60
ggcgaaggct tcctctgtg                                                 79
```